United States Patent
Cai et al.

(10) Patent No.: US 10,829,790 B2
(45) Date of Patent: *Nov. 10, 2020

(54) **RECOMBINANT *E. COLI* AND METHOD OF PRODUCING DANSHENSU BY USING SAME**

(71) Applicant: Jiangnan University, Wuxi (CN)

(72) Inventors: Yujie Cai, Wuxi (CN); Tianzhen Xiong, Wuxi (CN); Jinbin Liu, Wuxi (CN); Yanrui Ding, Wuxi (CN); Yajun Bai, Wuxi (CN); Xiaohui Zheng, Wuxi (CN)

(73) Assignee: Jiangnan University, Wuxi (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/536,406

(22) Filed: Aug. 9, 2019

(65) Prior Publication Data

US 2019/0360007 A1 Nov. 28, 2019

Related U.S. Application Data

(63) Continuation of application No. PCT/CN2018/111884, filed on Oct. 25, 2018.

(30) Foreign Application Priority Data

Apr. 19, 2018 (CN) .......................... 2018 1 0352668
Apr. 19, 2018 (CN) .......................... 2018 1 0352680
Apr. 19, 2018 (CN) .......................... 2018 1 0352697
Apr. 19, 2018 (CN) .......................... 2018 1 0352742

(51) Int. Cl.
*C12P 7/42* (2006.01)
*C12N 1/20* (2006.01)

(52) U.S. Cl.
CPC .................. *C12P 7/42* (2013.01); *C12N 1/20* (2013.01); *C12Y 101/01027* (2013.01); *C12Y 101/01047* (2013.01); *C12Y 104/01002* (2013.01); *C12Y 104/03002* (2013.01); *C12Y 401/99002* (2013.01)

(58) Field of Classification Search
None
See application file for complete search history.

(56) References Cited

FOREIGN PATENT DOCUMENTS

| CN | 101565694 A | 10/2009 |
|---|---|---|
| CN | 103667371 A | 3/2014 |
| CN | 107299072 A | 10/2017 |
| CN | 107916245 A | 4/2018 |

OTHER PUBLICATIONS

Findrik et al. Chem. Biochem. Eng. Q., 19 (4) (2005), pp. 351-358 (Year: 2005).*
Poljanac et al. Enzymatic preparation of Danshensu. Slovenski Kemijski Dnevi, Maribor, Slovenia, Sep. 25-26, 2003 (2003), 239-245. Univerza v Mariboru, Fakulteta za Kemijo in Kemijsko Tehnologijo: Maribor, Slovenia (Year: 2003).*
Kizer et al. Appl Environ Microbiol. May 2008;74(10):3229-41. (Year: 2008).*
Prather et al. Curr Opin Biotechnol. Oct. 2008;19(5):468-74. (Year: 2008).*
Sheng et al. PLoS One. Aug. 4, 2014;9(8):e104204 (Year: 2014).*
Nural et al. Mol Biotechnol. Apr. 2016;58(4):256-67 (Year: 2016).*
Accession Q05353. Nov. 1, 1995 (Year: 1995).*
Accession P11458. Oct. 1, 1989 (Year: 1989).*
Liu et al. Appl Biochem Biotechnol. Aug. 2009;158(2):313-22 (Year: 2009).*
Kim et al. J Microbiol Biotechnol. Jan. 2007;17(1):116-22 (Year: 2007).*
Vargas et al. Int J Biol Macromol. Aug. 2014;69:200-7. (Year: 2014).*

* cited by examiner

*Primary Examiner* — Christian L Fronda
(74) *Attorney, Agent, or Firm* — IPro, PLLC

(57) ABSTRACT

The present disclosure discloses a production method of Danshensu, belonging to the technical field of bioengineering. The present disclosure constructs a novel genetic engineering strain co-expressed by three enzymes, which can be applied to the production of optically pure 3-(3,4-dihydroxyphenyl)-2-hydroxypropionic acid. All of the (D/L)-α-hydroxycarboxylic acid dehydrogenase selected by the present disclosure have the characteristics of poor substrate specificity and strong optical specificity, and can produce optically pure D-danshensu and L-danshensu. Further, the production efficiency of the recombinant strain is improved by knocking out or enhancing the expression of a related gene on the *E. coli* genome to promote substrate transport and reduce product decomposition. The method for producing Danshensu and α-ketoglutaric acid by using the transformation of the recombinant strain according to the present disclosure is simple, has easily available raw materials, few impurities, and has good industrial application prospects.

7 Claims, No Drawings

Specification includes a Sequence Listing.

SEQUENCE LISTING

<160> NUMBER OF SEQ ID NOS: 26

<210> SEQ ID NO 1
<211> LENGTH: 20
<212> TYPE: DNA
<213> ORGANISM: Artificial Sequence
<220> FEATURE:
<223> OTHER INFORMATION: Synthetic DNA

<400> SEQUENCE: 1
ttatggcttc accaatgcga                                               20

<210> SEQ ID NO 2
<211> LENGTH: 20
<212> TYPE: DNA
<213> ORGANISM: Artificial Sequence
<220> FEATURE:
<223> OTHER INFORMATION: Synthetic DNA

<400> SEQUENCE: 2
ttaacggcgt cggcttcggg                                               20

<210> SEQ ID NO 3
<211> LENGTH: 25
<212> TYPE: DNA
<213> ORGANISM: Artificial Sequence
<220> FEATURE:
<223> OTHER INFORMATION: Synthetic DNA

<400> SEQUENCE: 3
taagggttac gttgacggtt aagca                                         25

<210> SEQ ID NO 4
<211> LENGTH: 50
<212> TYPE: DNA
<213> ORGANISM: Artificial Sequence
<220> FEATURE:
<223> OTHER INFORMATION: Synthetic DNA

<400> SEQUENCE: 4
tcggccactc atcaacatga ttcattgctt aaccgtcaac gtaacccta               50

<210> SEQ ID NO 5
<211> LENGTH: 50
<212> TYPE: DNA
<213> ORGANISM: Artificial Sequence
<220> FEATURE:
<223> OTHER INFORMATION: Synthetic DNA

<400> SEQUENCE: 5
taagggttac gttgacggtt aagcaatgaa tcatgttgat gagtggccga              50

<210> SEQ ID NO 6
<211> LENGTH: 50
<212> TYPE: DNA
<213> ORGANISM: Artificial Sequence
<220> FEATURE:
<223> OTHER INFORMATION: Synthetic DNA

<400> SEQUENCE: 6
ttgctaaagt atcgagatga aacatggttt tctcctgtca ggaacgttcg              50

<210> SEQ ID NO 7
<211> LENGTH: 50
<212> TYPE: DNA
<213> ORGANISM: Artificial Sequence

```
<220> FEATURE:
<223> OTHER INFORMATION: Synthetic DNA

<400> SEQUENCE: 7
cgaacgttcc tgacaggaga aaaccatgtt tcatctcgat actttagcaa              50

<210> SEQ ID NO 8
<211> LENGTH: 25
<212> TYPE: DNA
<213> ORGANISM: Artificial Sequence
<220> FEATURE:
<223> OTHER INFORMATION: Synthetic DNA

<400> SEQUENCE: 8
agccagctcc cacagtttca gcccc                                        25

<210> SEQ ID NO 9
<211> LENGTH: 25
<212> TYPE: DNA
<213> ORGANISM: Artificial Sequence
<220> FEATURE:
<223> OTHER INFORMATION: Synthetic DNA

<400> SEQUENCE: 9
tcgaatcctg cacgacccac cacta                                        25

<210> SEQ ID NO 10
<211> LENGTH: 50
<212> TYPE: DNA
<213> ORGANISM: Artificial Sequence
<220> FEATURE:
<223> OTHER INFORMATION: Synthetic DNA

<400> SEQUENCE: 10
tcggccactc atcaacatga ttcatcgaca ttagcgtaat attcgctgtt              50

<210> SEQ ID NO 11
<211> LENGTH: 50
<212> TYPE: DNA
<213> ORGANISM: Artificial Sequence
<220> FEATURE:
<223> OTHER INFORMATION: Synthetic DNA

<400> SEQUENCE: 11
aacagcgaat attacgctaa tgtcgatgaa tcatgttgat gagtggccga              50

<210> SEQ ID NO 12
<211> LENGTH: 50
<212> TYPE: DNA
<213> ORGANISM: Artificial Sequence
<220> FEATURE:
<223> OTHER INFORMATION: Synthetic DNA

<400> SEQUENCE: 12
tgtctggatc aaacattacg ctcatggttt tctcctgtca ggaacgttcg              50

<210> SEQ ID NO 13
<211> LENGTH: 50
<212> TYPE: DNA
<213> ORGANISM: Artificial Sequence
<220> FEATURE:
<223> OTHER INFORMATION: Synthetic DNA

<400> SEQUENCE: 13
cgaacgttcc tgacaggaga aaaccatgag cgtaatgttt gatccagaca              50
```

<210> SEQ ID NO 14
<211> LENGTH: 25
<212> TYPE: DNA
<213> ORGANISM: Artificial Sequence
<220> FEATURE:
<223> OTHER INFORMATION: Synthetic DNA

<400> SEQUENCE: 14
catccacgga caatgcgcgc agctg                                     25

<210> SEQ ID NO 15
<211> LENGTH: 1100
<212> TYPE: DNA
<213> ORGANISM: Artificial Sequence
<220> FEATURE:
<223> OTHER INFORMATION: Synthetic DNA

<400> SEQUENCE: 15
atgaatcatg ttgatgagtg gccgatcgct acgtgggaag aaaccacgaa actccattgc    60
gcaatacgct gcgataacca gtaaaaagac cagccagtga atgctgattt gtaaccttga   120
atatttattt tccataacat ttcctgcttt aacataattt tccgttaaca taacgggctt   180
ttctcaaaat ttcattaaat attgttcacc cgttttcagg taatgactcc aacttattga   240
tagtgtttta tgttcagata atgcccgatg actttgtcat gcagctccac cgattttgag   300
aacgacagcg acttccgtcc cagccgtgcc aggtgctgcc tcagattcag gttatgccgc   360
tcaattcgct gcgtatatcg cttgctgatt acgtgcagct ttcccttcag gcgggattca   420
tacagcggcc agccatccgt catccatatc accacgtcaa agggtgacag caggctcata   480
agacgcccca gcgtcgccat agtgcgttca ccgaatacgt gcgcaacaac cgtcttccgg   540
agcctgtcat acgcgtaaaa cagccagcgc tggcgcgatt tagccccgac atagccccac   600
tgttcgtcca tttccgcgca gacgatgacg tcactgcccg gctgtatgcg cgaggttacc   660
gactgcggcc tgagtttttt aagtgacgta aaatcgtgtt gaggccaacg cccataatgc   720
gggcagttgc ccggcatcca acgccattca tggccatatc aatgattttc tggtgcgtac   780
cgggttgaga agcggtgtaa gtgaactgca gttgccatgt tttacggcag tgagagcaga   840
gatagcgctg atgtccggcg gtgcttttgc cgttacgcac caccccgtca gtagctgaac   900
aggagggaca gctgatagaa acagaagcca ctggagcacc tcaaaaacac catcatacac   960
taaatcagta agttggcagc atcaccccgt tttcagtacg ttacgtttca ctgtgagaat  1020
ggagattgcc catcccgcca tcctggtcta agcctggaaa ggatcaattt tcatccgaac  1080
gttcctgaca ggagaaaacc                                            1100

<210> SEQ ID NO 16
<211> LENGTH: 20
<212> TYPE: DNA
<213> ORGANISM: Artificial Sequence
<220> FEATURE:
<223> OTHER INFORMATION: Synthetic DNA

<400> SEQUENCE: 16
tatgcccgtc gatcgcgccc                                           20

<210> SEQ ID NO 17
<211> LENGTH: 120
<212> TYPE: DNA
<213> ORGANISM: Artificial Sequence
<220> FEATURE:
<223> OTHER INFORMATION: Synthetic DNA

<400> SEQUENCE: 17
ccaagatcac gcacgtaccg tcgatgtatc tctctgaact gccagggaaa aaccacggtt      60
agatcagcaa gcgttgccgg gaaatgggcg tcgataccat tatcgttttc gacacccact    120

<210> SEQ ID NO 18
<211> LENGTH: 20
<212> TYPE: DNA
<213> ORGANISM: Artificial Sequence
<220> FEATURE:
<223> OTHER INFORMATION: Synthetic DNA

<400> SEQUENCE: 18
tcatcgagta cctcttgcgc      20

<210> SEQ ID NO 19
<211> LENGTH: 120
<212> TYPE: DNA
<213> ORGANISM: Artificial Sequence
<220> FEATURE:
<223> OTHER INFORMATION: Synthetic DNA

<400> SEQUENCE: 19
tagcctgata tgcacgctta tcttcactgt ctttcccact cgccgctggt gggatatgtc      60
aatggcgtga ttgccagcgc ccgcgagcgt attgcggctt ctcccctga actggtggtg    120

<210> SEQ ID NO 20
<211> LENGTH: 20
<212> TYPE: DNA
<213> ORGANISM: Artificial Sequence
<220> FEATURE:
<223> OTHER INFORMATION: Synthetic DNA

<400> SEQUENCE: 20
cagcacacac ccttcttgcg      20

<210> SEQ ID NO 21
<211> LENGTH: 25
<212> TYPE: DNA
<213> ORGANISM: Artificial Sequence
<220> FEATURE:
<223> OTHER INFORMATION: Synthetic DNA

<400> SEQUENCE: 21
aaggtctaat gaggagatat ttatg      25

<210> SEQ ID NO 22
<211> LENGTH: 50
<212> TYPE: DNA
<213> ORGANISM: Artificial Sequence
<220> FEATURE:
<223> OTHER INFORMATION: Synthetic DNA

<400> SEQUENCE: 22
tcggccactc atcaacatga ttcatcataa atatctcctc attagacctt      50

<210> SEQ ID NO 23
<211> LENGTH: 50
<212> TYPE: DNA
<213> ORGANISM: Artificial Sequence
<220> FEATURE:
<223> OTHER INFORMATION: Synthetic DNA

<400> SEQUENCE: 23

```
<210> SEQ ID NO 24
<211> LENGTH: 50
<212> TYPE: DNA
<213> ORGANISM: Artificial Sequence
<220> FEATURE:
<223> OTHER INFORMATION: Synthetic DNA

<400> SEQUENCE: 24
tatgtatgcc gcgtatcagc ttcatggttt tctcctgtca ggaacgttcg            50

<210> SEQ ID NO 25
<211> LENGTH: 50
<212> TYPE: DNA
<213> ORGANISM: Artificial Sequence
<220> FEATURE:
<223> OTHER INFORMATION: Synthetic DNA

<400> SEQUENCE: 25
cgaacgttcc tgacaggaga aaaccatgaa gctgatacgc ggcatacata            50

<210> SEQ ID NO 26
<211> LENGTH: 25
<212> TYPE: DNA
<213> ORGANISM: Artificial Sequence
<220> FEATURE:
<223> OTHER INFORMATION: Synthetic DNA

<400> SEQUENCE: 26
ttcatcacgc gcaatctgcg ctttc            25
```

RECOMBINANT *E. COLI* AND METHOD OF PRODUCING DANSHENSU BY USING SAME

TECHNICAL FIELD

The present disclosure relates to a production method of Danshensu, belonging to the technical field of bioengineering.

BACKGROUND

Danshensu extracted from Salvia miltiorrhiza, scientific name: R-(+)-3-(3,4-dihydroxyphenyl)-2-hydroxypropionic acid, D-(+)-β-(3,4-dihydroxyphenyl)lactic acid, English name: Danshensu, D-DSS, R-DSS, (R)-(+)-3-(3,4-dihydroxyphenyl)-lactic acid, (R)-(+)-3-(3,4-dihydroxyphenyl)-2-hydroxypropanoic acid, is a dextrorotatory phenolic acid compound. No natural levorotatory Danshensu exists currently.

Danshensu is an important active ingredient in the water extract of Salvia miltiorrhiza. It was obtained from the water extract of Salvia miltiorrhiza in 1980 at home and the structure was identified (Study on the water-soluble active ingredients of Salvia miltiorrhiza, the structure of II.D(+)β (3,4-dihydroxyphenyl)lactic acid, Journal of Shanghai First Medical College, 1980, 05(7), 384-385). Various studies have shown that Danshensu has important pharmacological effects and has a unique therapeutic effect on the treatment of cardiovascular and cerebrovascular diseases, etc.

At present, Danshensu is mainly extracted from Salvia miltiorrhiza (Patent No. CN200810038853.9). The content of Danshensu in Salvia miltiorrhiza is low, the cost of planting Salvia miltiorrhiza is high and the yield is limited. Therefore, Danshensu is not only expensive but also far from meeting the market demand. Patent No. CN201310559498.0 proposes a method for producing Danshensu through glucose fermentation by constructing *Escherichia coli* genetically engineering strain. Since the anabolic pathway involves the use of hydroxylase, the enzyme easily oxidizes a product of metabolic process and affects the yield of Danshensu. At the same time, since *E. coli* fermentation is a high oxygen consumption process, it also oxidizes Danshensu, the current method has lower yield and the cost will be higher than the plant extraction process. Patent No. CN201210190171.6 proposes a method for producing Danshensu by hydrolyzing salvianolic acid B. Salvianolic acid B needs to be extracted from Salvia miltiorrhiza, and there are a large number of side reactions in the chemical hydrolysis process, which is also not suitable for large-scale production. A catalyst used for chiral synthesis of Danshensu (Patent No. CN201210420488.4) is extremely expensive and currently only stays at the laboratory level.

As early as 1988, Roth et al. proposed a method in which levodopa was firstly treated with a chemical method to obtain corresponding 3,4-dihydroxyphenylpyruvic acid, and then S-(+)-3-(3,4-dihydroxyphenyl)-2-hydroxypropionic acid (S-DSS, L-DSS) was synthesized by a enzymatic method (Enzymatic Synthesis of (S)-(−)-3-(3,4-dihydroxyphenyl)lactic Acid, Arch. Pharm. (Weinheim) 321, 179-180 (1988)). Z. Findrik, et al. used snake venom amino acid oxidase to convert levodopa into 3,4-dihydroxyphenylpyruvic acid which was then reduced to generate D-(3,4-dihydroxyphenyl)lactic acid by D-lactate dehydrogenase (Modelling and Optimization of the (R)-(+)-3,4-dihydroxyphenyllactic Acid Production Catalyzed with D-lactate Dehydrogenase from *Lactobacillus* leishmannii Using Genetic Algorithm, Chem. Biochem. Eng. Q. 19(4) 351-58 (2005)). The preparation of the 3,4-dihydroxyphenylpyruvic acid intermediate by these two methods is costly and complicated in operation.

SUMMARY

Based on the defects of various current methods, the present disclosure provides a production method for optically pure Danshensu, and constructs an engineering strain by co-expressing multiple enzymes, thereby realizing efficient production of Danshensu. The present disclosure provides a recombinant strain capable of producing Danshensu at a low cost. At the same time, the present disclosure addresses the technical problems of the construction and application of the strain.

The present disclosure provides a recombinant strain capable to produce an optical pure Danshensu at a low cost; the recombinant strain simultaneously expresses an α-hydroxycarboxylic acid dehydrogenase and an L-amino acid oxidase, and any one of the following: an exogenous L-glutamate dehydrogenase, an exogenous L-lactate dehydrogenase, a glucose dehydrogenase, and a tyrosine phenol lyase, wherein the tyrosine phenol lyase and the L-lactate dehydrogenase are simultaneously expressed; and a gene related to the decomposition of phenolic compounds is knocked out on the basis of an *E. coli* host.

In one embodiment, the α-hydroxycarboxylic acid dehydrogenase is a D-type α-hydroxycarboxylic acid dehydrogenase from *Lactobacillus plantarum* ATCC 14917, *Enterococcus faecalis* ATCC 35038 or *Lactobacillus fermentum* ATCC 14931.

In one embodiment, the α-hydroxycarboxylic acid dehydrogenase is an L-type α-hydroxycarboxylic acid dehydrogenase from *Bacillus coagulans* DSM 1, *Weissella confusa* strain DSM 20196 or *Lactobacillus fermentum* ATCC 14931.

In one embodiment, the α-hydroxycarboxylic acid dehydrogenase is D-α-hydroxycarboxylic acid dehydrogenase, and the amino acid sequence thereof is a sequence of accession NO. WP_003643296.1, WP_002335374.1, or EE122188.1 in NCBI; the α-hydroxycarboxylic acid dehydrogenase is an L-α-hydroxycarboxylic acid dehydrogenase, and the amino acid sequence thereof is a sequence of accession NO. WP_013858488.1, WP_003607654.1 or WP_035430779.1 in NCBI.

In one embodiment, the nucleotide sequence of the D-α-hydroxycarboxylic acid dehydrogenase is a sequence of accession NO. NZ_GL379761 REGION: COMPLEMENT (533562 . . . 534560), NZ_KB944641 REGION: 161892 . . . 162830, or ACGI01000078 REGION: 20793 . . . 21791 in NCBI; the nucleotide sequence of L-α-hydroxycarboxylic acid dehydrogenase is a sequence of accession NO. NZ_ATUM01000014 REGION: 39316 . . . 40254, NZ_JQAY01000006 REGION: 69708 . . . 70640, or NZ_GG669901 REGION: 45517 . . . 46470 in NCBI.

In one embodiment, the L-glutamate dehydrogenases are from *E. coli* BL21, *Rhodobacter sphaeroides* ATCC BAA-808, *Clostridium symbiosum* ATCC 14940, and *Bacillus subtilis* 168.

In one embodiment, the amino acid sequence of the L-glutamate dehydrogenases are a sequence of accession NO. WP_000373021.1, WP_011338202.1, WP_003497202.1, or WP_010886557.1 in NCBI.

In one embodiment, the nucleotide sequence of the L-glutamate dehydrogenases are a sequence of accession NO: NC_012892 REGION: 1786741 . . . 1788084, NC_007493 REGION: complement (2129131 . . . 2130558), NZ_KE992901 REGION: complement (17603 . . . 18955), or NC_000964 REGION: complement (2402067 . . . 2403350) in NCBI.

In one embodiment, the L-amino acid oxidases are not production of hydrogen peroxide from ProteusProteus mirabilis ATCC 29906, Cosenzaea myxofaciens ATCC 19692, MorganellaMorganella morganii ATCC 49993, ProvidenciaProvidencia rettgeri DSM 1131 or Ignatzschineria larvae DSM 13226.

In one embodiment, the amino acid sequences of the L-amino acid oxidase are sequence of accession NO. WP_004244224.1, OAT30925.1, EFE55026.1, WP_036414800.1, or WP_026879504.1 in NCBI.

In one embodiment, the nucleotide sequences of the L-amino acid oxidase are: NZ_GG668576 REGION: 1350390 . . . 1351805, LXEN01000066 REGION: 20563 . . . 21963, ACCI02000030 REGION: 21025 . . . 22443, NZ_LAGC01000006 REGION: 309569 . . . 310993, or NZ_KI783332 REGION: 35799 . . . 37217 as in the sequence listing.

In one embodiment, the L-lactate dehydrogenase is from Lactococcus lactis ATCC 19257.

In one embodiment, the amino acid sequence of the L-lactate dehydrogenase is a sequence of accession NO. WP_003131075.1 in NCBI.

In one embodiment, the nucleotide sequence of the L-lactate dehydrogenase is a sequence of accession NO. NZ_JXJZ01000017 REGION: 18532 . . . 19509 in NCBI.

In one embodiment, the tyrosine phenol lyase is from Erwinia herbicola ATCC 214344.

In one embodiment, the amino acid sequence of the tyrosine phenol lyase is a sequence of accession NO. P31011.2 in NCBI.

In one embodiment, the glucose dehydrogenase is from Bacillus subtilis ATCC 13952.

In one embodiment, the amino acid sequence of the glucose dehydrogenase is a sequence of accession NO. WP_013351020.1 in NCBI.

In one embodiment, the nucleotide sequence of the glucose dehydrogenase is a sequence of accession NO. NZ_CP009748 REGION: 386154 . . . 38693 in NCBI.

In one embodiment, the recombinant strain is a recombinant engineering strain obtained by ligating all the genes encoding L-amino acid oxidase, α-hydroxycarboxylic acid dehydrogenase, and L-glutamate dehydrogenase to a plasmid to construct a recombinant plasmid co-expressed by three genes, and then transforming the recombinant plasmid into the corresponding strain.

In one embodiment, the recombinant strain is a recombinant engineering strain obtained by ligating all the genes encoding L-amino acid oxidase, α-hydroxycarboxylic acid dehydrogenase, and L-lactate dehydrogenase to a plasmid to construct a recombinant plasmid co-expressed by three genes, and then transforming the recombinant plasmid into the corresponding strain.

In one embodiment, the recombinant strain is a recombinant engineering strain obtained by ligating all the genes encoding tyrosine phenol lyase, L-amino acid oxidase, α-hydroxycarboxylic acid dehydrogenase, and L-lactate dehydrogenase to two plasmids and then transforming the recombinant plasmid into E. coli host.

In one embodiment, the α-hydroxycarboxylic acid dehydrogenase gene and the L-lactate dehydrogenase gene are expressed after ligation to the plasmid pETDuet-1, the L-amino acid oxidase and the tyrosine phenol lyase genes are expressed after ligation to plasmid pACYCDue-1.

In one embodiment, the recombinant strain is a recombinant engineering strain obtained by ligating all the genes encoding L-amino acid oxidase, α-hydroxycarboxylic acid dehydrogenase, and glucose dehydrogenase to a plasmid to construct a recombinant plasmid co-expressed by three genes, and then transforming the recombinant plasmid into the corresponding strain.

In one embodiment, the recombinant strain is constructed using E. coli BL21 (DE3) as a host.

In one embodiment, the gene related to the decomposition of the phenolic compound is any one or a combination of hpaD and mhpB.

In one embodiment, the nucleotide sequence of the genes related to the decomposition of the phenolic compound are sequence of accession NO. NC_012892 REGION: complement (4505585 . . . 4506436) and NC_012892 REGION: 339806 . . . 340750 in NCBI.

In one embodiment, the recombinant E. coli further enhances expression of one or more of a glutamate transporter gene, a lactate transporter gene, a catechol transporter gene, an NAD synthesis gene, and an FAD synthesis gene; wherein, the catechol transporter gene and the lactate transporter gene are expressed simultaneously, and the glutamate transporter gene and the lactate transporter gene are expressed at different times.

In one embodiment, the enhanced expression is realized by adding a constitutive promoter in front of the gene needing enhanced expression on the E. coli BL21 (DE3) genome.

In one embodiment, the gene with enhanced expression is any one or more of gltS (glutamate transporter gene), nadA (NAD synthesis gene), and ribF (FAD synthesis gene).

In one embodiment, the gltS is a sequence of accession NO. NC_012892 REGION: complement (3694931 . . . 3696136) in NCBI; nadA is a sequence of accession NO. NC_012892 REGION: 740487 . . . 741530 in NCBI; and ribF is a sequence of accession NO. NC_012892 REGION: 25479 . . . 26420 in NCBI.

In one embodiment, the gene with enhanced expression are any one or more of lldP (lactate transporter gene), nadA (NAD synthesis gene), and ribF (FAD synthesis gene).

In one embodiment, the lldP is a sequence of accession NO. NC_012892 REGION: 3646638 . . . 3648293 in NCBI; nadA is a sequence of accession NO. NC_012892 REGION: 740487 . . . 741530 in NCBI; and ribF is a sequence of accession NO. NC_012892 REGION: 25479 . . . 26420 in NCBI.

In one embodiment, the genes with enhanced expression are any one or more of lldP (lactate transporter gene), hpaX (catechol transporter gene), mhpT (catechol transporter gene), nadA (NAD synthesis gene), pdxJ (pyridoxal phosphate synthesis gene) and ribF (FAD synthesis gene).

In one embodiment, the lldP is a sequence of accession NO. NC_012892 REGION: 3646638 . . . 3648293 in NCBI; hpaX is a sequence of accession NO. NC_012892 REGION: complement (4502025 . . . 4503401) in NCBI; mhpT is a sequence of accession NO. NC_012892 REGION: 344788 . . . 345999 in NCBI; nadA is a sequence of accession NO. NC_012892 REGION: 740487 . . . 741530 in NCBI; pdxJ is a sequence of accession NO. NC_012892 REGION: complement (2567591 . . . 2568322) in NCBI; and ribF is a sequence of accession NO. NC_012892 REGION: 25479 . . . 26420 in NCBI.

In one embodiment, the recombinant strain enhances expression of lldP, hpaX, mhpT, nadA, pdxJ, and ribF, and simultaneously expresses tyrosine phenol lyase, L-amino acid oxidase, L-lactate dehydrogenase and α-hydroxycarboxylic acid dehydrogenase based on an *E. coli* host that knocks out hpaD and mhpB.

The present disclosure provides a method for producing Danshensu using the recombinant strain.

In one embodiment, Danshensu is produced by whole cell transformation.

In one embodiment, when the recombinant *E. coli* simultaneously expresses the α-hydroxycarboxylic acid dehydrogenase, the L-amino acid oxidase, and the exogenous L-glutamate dehydrogenase, the whole cell transformation production system includes 1-200 g/L of wet cell weight, 1-200 g/L of levodopa, 1-200 g/L of L-glutamic acid, pH 6.0-9.0; and the reaction is performed at 15-40° C. for 1-48 hours.

In one embodiment, when the recombinant *E. coli* simultaneously expresses the α-hydroxycarboxylic acid dehydrogenase, the L-amino acid oxidase, and the exogenous L-lactate dehydrogenase, the whole cell transformation production system includes 1-200 g/L of wet cell weight, levodopa in a concentration of 1-200 g/L, L-lactic acid in a concentration of 1-200 g/L, pH 4.0-9.0; and the reaction is performed at 15-40° C. for 1-48 hours.

In one embodiment, when the recombinant *E. coli* simultaneously expresses the α-hydroxycarboxylic acid dehydrogenase, the L-amino acid oxidase, a tyrosine phenol lyase, and the L-lactate dehydrogenase, the whole cell transformation production system includes 1-200 g/L of wet cell weight, catechol in a concentration of 1-200 g/L, L-lactic acid in a concentration of 1-200 g/L, pH 6.0-9.0, and ammonium ion in a concentration of 1-30 g/L; and the reaction is performed at 15-40° C. for 1-48 hours. After the transformation, the yield and configuration of Danshensu are determined by liquid chromatography.

In one embodiment, when the recombinant *E. coli* simultaneously expresses the α-hydroxycarboxylic acid dehydrogenase, the L-amino acid oxidase, and the glucose dehydrogenase, the whole cell transformation production system includes 1-200 g/L of wet cell weight, levodopa in a concentration of 1-200 g/L, glucose in a concentration of 1-200 g/L, pH 6.0-9.0; and the reaction is performed at 15-40° C. for 1-48 hours.

The present disclosure provides the application of the recombinant strains of the present disclosure or the methods of the present disclosure in the fields of chemical industry, food, medicines, and the like.

The present disclosure constructs a novel genetic engineering strain by co-expressing three enzymes, which can be applied to the production of optically pure 3-(3,4-dihydroxyphenyl)-2-hydroxypropionic acid. All of the (D/L)-α-hydroxycarboxylic acid dehydrogenase selected by the present disclosure have the characteristics of poor substrate specificity and strong optical specificity, and can produce optically pure D-danshensu and L-danshensu. Further, the production efficiency of the recombinant strain is improved by knocking out or enhancing the expression of the related genes on the *E. coli* genome to promote substrate transport and reduce product decomposition. The method for producing Danshensu and α-ketoglutaric acid by using *E.coli* whole cells according to the present disclosure is simple, has easily available raw materials, and has good industrial application prospects.

DETAILED DESCRIPTION

The core function of the engineering strain according to the present disclosure is that a plurality of enzymes can be simultaneously expressed, which respectively are L-amino acid oxidase and α-hydroxycarboxylic acid dehydrogenase and any one of the following: exogenous L-glutamate dehydrogenase, exogenous L-lactate dehydrogenase, glucose dehydrogenase, tyrosine phenol lyase, and L-lactate dehydrogenase, wherein the tyrosine phenol lyase and the L-lactate dehydrogenase are simultaneously expressed. The principle is that in the whole cell of the engineering strain, any one of L-glutamate dehydrogenase, L-lactate dehydrogenase, and glucose dehydrogenase will produce corresponding α-ketoglutaric acid, pyruvic acid, gluconic acid and NADH by dehydrogenating the corresponding L-glutamic acid, L-lactic acid, and glucose using the NAD in the strain as a coenzyme; the tyrosine phenol lyase produces levodopa by catalyzing pyruvic acid, ammonium ion and catechol; the levodopa is deaminated to generate 3,4-dihydroxyphenylpyruvic acid by the L-amino acid oxidase; the α-hydroxycarboxylic acid dehydrogenase reduces the 3,4-dihydroxyphenylpyruvic acid to Danshensu using NADH which is produced by dehydrogenation of glutamic acid and the coenzyme of NAD is regenerated simultaneously. The transport of the substrate is promoted and the decomposition of the product is reduced by knocking out or enhancing the expression of the related genes on the *E. coli* genome simultaneously, and thus the yield of the target product is increased.

1. Strains and Plasmids Involved by the Present Disclosure

*Lactobacillus plantarum* ATCC 14917, *Enterococcus faecalis* ATCC 35038, *Lactobacillus fermentum* ATCC 14931, *Bacillus subtilis* ATCC 13952, *E. coli* BL21 (DE3), *Proteus mirabilis* ATCC 29906, *Cosenzaea myxofaciens* ATCC 19692, *MorganellaMorganella morganii* ATCC 49993 *Lactococcus lactis* ATCC 19257, *Erwinia herbicola* ATCC 214344, and *Aeromonas phenologenes* ATCC 7966 purchased from the American Type Culture Collection (ATCC). *Bacillus coagulans* DSM 1, *Weissella confusa* strain DSM 20196, *ProvidenciaProvidencia rettgeri* DSM 1131, and *Ignatzschineria larvae* DSM 13226 purchased from the German Collection of Microorganisms and Cell Cultures (DSMZ). PETDuet-1, pACYCDue-1, pCOLADuet-1, pRSFDuet-1 plasmid and *E. coli* BL21 (DE3) purchased from Novagen. pCasRed and pCRISPR-gDNA purchased from Zhenjiang Aibimeng Biotechnology Co., Ltd.

2. Knockout and Constitutive Enhanced Expression of Related Genes in *E. coli*

(1) Knockout of Genes Related to the Decomposition of Phenolic Compounds in *E. coli*

The phenolic substances according to the present disclosure are highly susceptible to decomposition by enzymes in *E. coli*, and the related genes are knocked out according to the literature (Biodegradation of Aromatic Compounds by *E. coli*, Microbiol Mol Biol Rev. 2001, 65(4): 523-569.) to avoid decomposition of products and substrates. The selected genes are hpaD and mhpB with NCBI accession NO. NC_012892 REGION: complement (4505585 . . . 4506436) and NC_012892 REGION: 339806 . . . 340750.

(2) Constitutive Enhanced Expression of Glutamate Transporter Gene in *E. coli*

The process of whole cell transformation cannot be performed until the substrates are transported into the cell. The enhanced glutamate transporter helps to maintain the high concentration of the intracellular substrate quickly and for a long time, which is beneficial to the performance of the reaction. The selected gene associated with glutamate transport is gltS with NCBI accession NO. NC_012892 REGION: complement (3694931 . . . 3696136). Dopa is similar to aromatic amino acids and needs to absorb amino acids and the like during cell culture. Therefore, the strains themselves express a large number of amino acid transporters without further enhancing expression.

(3) Constitutive Enhanced Expression of Key Genes Related to Coenzyme Synthesis in *E. coli*

In the reduction process of α-hydroxycarboxylic acid dehydrogenase, it is necessary to use NADH as a coenzyme. NAD level in the strain can be improved by enhancing the expression of key enzymes in the NAD synthesis pathway of *E. coli*, which is beneficial to the formation of Danshensu. The selected gene is nadA with NCBI accession NO. NC_012892 REGION: 740487 . . . 741530.

FAD is a coenzyme of L-amino acid oxidase. Overexpressing the important gene ribF in the coenzyme pathway is beneficial to strengthen L-amino acid oxidase activity. The accession NO in NCBI is: NC_012892 REGION: 25479 . . . 26420.

3. Selection of Enzyme (1) Selection of L-Amino Acid Oxidase

L-amino acid oxidase widely exists in bacteria, fungi, mammalian cells, snake venom, insect toxins and algae (L-amino acid oxidase as biocatalyst: a dream too far. Appl. Microbiol. Biotechnol. 2013, 97:9323-41). L-amino acid oxidase transfers hydrogen on the α-amino group and α-carbon atom to the FAD, and most of which directly oxidize reduced FAD using the molecular oxygen to produce the oxidized FAD, and simultaneously hydrogen peroxide is produced. For example, Poljanac et al. oxidized dopa to produce 3,4-dihydroxyphenylpyruvic acid using the snake venom L-amino acid oxidase of *Crotalus adamanteus*, followed by adding lactate dehydrogenase and formate dehydrogenase to generate 3,4-dihydroxyphenyl lactic acid. In addition, catalase must be added during this process to eliminate the toxicity of hydrogen peroxide (Modelling and Optimization of the (R)-(+)-3,4-Dihydroxyphenyllactic Acid Production Catalyzed, Chem. Biochem. Eng. Q.2005, 19 (4) 351-358). There is also a class of L-amino acid oxidases associated with electron transport chains on the cell membrane. Electrons are transported to the cytochrome oxidase via the respiratory chain, reducing molecular oxygen to water, thereby not generating hydrogen peroxide. This enzyme is mainly present in bacteria such as *Proteus* sp., *Providencia* sp., *Morganella* sp., etc. (Crystal structure of a membrane-bound l-amino acid deaminase from *Proteus vulgaris*. J. Struct Biol. 2016, 195: 306-15). The present disclosure selects five L-amino acid oxidases which do not produce hydrogen peroxide, and L-amino acid oxidase genes pmaao, cmaao, praao, mmaao, and ilaao are cloned from *Proteus mirabilis* ATCC 29906, *Cosenzaea myxofaciens* ATCC 19692, *Providencia rettgeri* DSM 1131, *Morganella morganii* ATCC 49993, *Ignatzschineria larvae* DSM 13226, respectively, the amino acid sequence of which are the sequences of accession NO. WP_004244224.1, OAT30925.1, EFE55026.1, WP_036414800.1 or WP_026879504.1 in NCBI. These enzymes are characterized by a wide range of substrates and strong activity.

(2) Selection of α-Hydroxycarboxylic Acid Dehydrogenase

According to the condition of the optimum substrate, the α-hydroxycarboxylic acid dehydrogenase includes lactate dehydrogenase, α-hydroxyisocaproate dehydrogenase, mandelic acid dehydrogenase, glyoxylate reductase, etc. These enzymes can act extensively on a variety of substrates to generate α-hydroxycarboxylic acids, and usually named after their optimum substrate. The present disclosure selects an enzyme which is highly optically active and has a strong activity against 3,4-dihydroxyphenylpyruvic acid for the production of D or L danshensu. The D-type α-hydroxycarboxylic acid dehydrogenase genes lpldhd, efmdhd, and lfldhd are cloned from *Lactobacillus plantarum* ATCC 14917, *Enterococcus faecalis* ATCC 35038, and *Lactobacillus fermentum* ATCC 14931, respectively, the amino acid sequence of which are the sequences of accession NO. WP_003643296.1, WP_002335374.1 and EEI22188.1 in NCBI. The L-type α-hydroxycarboxylic acid dehydrogenase genes bcldhl, wcldhl and Ifldhl are cloned from *Bacillus coagulans* DSM 1, *Weissella confusa* strain DSM 20196 and *Lactobacillus fermentum* ATCC 14931, respectively, the amino acid sequence of which are the sequences of accession NO. WP_013858488.1, WP_003607654.1, WP_035430779.1 in NCBI.

(3) Selection of L-Glutamate Dehydrogenase

L-glutamic acid is the most inexpensive amino acid. The α-ketoglutaric acid generated by dehydrogenation has a high added value. Currently, L-glutamic acid oxidase is mainly used for oxidizing L-glutamic acid to produce α-ketoglutaric acid, and in this process, hydrogen removed from L-glutamic acid is wasted. L-glutamate dehydrogenase widely exists in almost all organisms, and L-glutamic acid is used as a substrate to transfer hydrogen generated on L-glutamic acid to coenzyme NAD or NADP to generate NADH or NADPH. NADH or NADPH can be used as the hydrogen donor of the aforementioned hydroxycarboxylic acid dehydrogenase. The present disclosure obtains the L-glutamic acid genes ecgdh (amino acid sequence WP_000373021.1), rsgdh (amino acid sequence WP_011338202.1), csgdh (amino acid sequence WP_003497202.1) and bsgdh (amino acid sequence WP_010886557.1) from *E. coli* BL21, *Rhodobacter sphaeroides* ATCC BAA-808, *Clostridium symbiosum* ATCC 14940, and *Bacillus subtilis* 168, respectively.

(4) Selection of L-Lactate Dehydrogenase

L-lactic acid is the most inexpensive organic acid, and pyruvic acid generated by dehydrogenation has a higher added value. At present, L-lactate oxidase is mainly used for oxidizing L-lactic acid to produce pyruvic acid, and in this process, the hydrogen removed from L-lactic acid is wasted. There are also methods for producing keto acid by yeast fermentation. L-lactate dehydrogenase widely exists in a variety of microorganisms, and L-lactic acid is used as a substrate to transfer hydrogen generated on L-lactic acid to coenzyme NAD or NADP to generate NADH or NADPH. NADH or NADPH can be used as the hydrogen donor of the aforementioned α-hydroxy acid dehydrogenase. In general, the lactate dehydrogenase with NADH (NADPH) as a coenzyme tends to synthesize lactic acid with pyruvic acid as a substrate, but when lactate is excessively introduced, some lactate dehydrogenase will remove hydrogen from lactic acid to form pyruvic acid.

The present disclosure obtains the L-lactate dehydrogenase gene llldh (amino acid sequence WP_003131075.1) from *Lactococcus lactis* ATCC 19257.

(5) Selection of Tyrosine Phenol Lase

Tyrosine phenol lyase (TPL, EC4.1.99.2) is also known as β-tyrosinase. The tyrosine phenol lyase can catalyze the β-elimination reaction of L-tyrosine to generate phenol, pyruvic acid and ammonia, and can also catalyze the β-elimination reaction of dopa to produce catechol, pyruvic acid and ammonia. The reaction is reversible, and catechol, pyruvic acid and ammonia can be catalyzed by the tyrosine phenol lyase to form L-dopa. In the present disclosure, the tyrosine phenol lyase gene ehtpl is cloned from *Erwinia herbicola* ATCC 214344, and the amino acid sequence thereof is P31011.2.

(6) Selection of Glucose Dehydrogenase

In the biotransformation reaction, α-hydroxycarboxylic acid dehydrogenase requires NADH and/or NADPH as coenzymes, and often uses formate dehydrogenase, glucose dehydrogenase, phosphite dehydrogenase, etc to regenerate NADH and/or NADPH. Glucose dehydrogenase is the most active compared to other enzymes. Therefore, the present disclosure obtains the glucose dehydrogenase gene bsgdh from *Bacillus subtilis* ATCC 13952 (amino acid sequence WP_013351020.1).

4. Construction of Co-Expression System and Culture of Cell

At present, there are multiple methods for co-expression of *E. coli* multi-gene (Strategy of multi-gene co-expression in *E. coli*, Journal of Chinese Biotechnology, 2012, 32(4): 117-122). The construction according to the present disclosure is performed using the method as described in Liu Xianglei (Produce Shikimic Acid and Resveratrol by modifying *E. coli* using Synthetic Biology Technology, 2016, Shanghai Institute of Pharmaceutical Industry, PhD thesis). T7 promoter and an RBS binding point are both contained in front of each gene. Theoretically, since each gene has T7 and RBS in front, the expression intensity of the gene is not significantly affected by the arrangement order. Three genes were included in each plasmid, and the constructed plasmid was heat-transferred into *E. coli* competent cells and plated on an antibiotic solid plate to obtain a positive transformant upon screening, i.e. recombinant *E. coli*. Culture of cells: according to the classical recombinant *E. coli* culture and induced expression protocol, recombinant *E. coli* is transferred to LB fermentation medium (peptone 10 g/L, yeast powder 5 g/L, NaCl 10 g/L) at a volume ratio of 2%. When the OD600 of cells reaches 0.6-0.8, IPTG is added to a final concentration of 0.4 mM, and culture is performed at 20° C. for 8 h to induce expression. After the induction of expression is completed, the cells are collected by centrifugation at 20° C. and 8000 rpm for 20 minutes.

5. Detection and Analysis of Sample

Quantitative analysis of Danshensu: The transformation liquid is detected and analyzed by a PerkinElmer Series 200 high performance liquid chromatographic instrument fitted with a refractive index detector. The chromatographic conditions are as follows: a mobile phase of methanol-0.1% formic acid/water (40:60), a Hanbang Megres C18 chromatographic column (4.6×250 mm, 5 μm), a flow rate of 1 ml/min, a column temperature of 30° C., and an injection volume of 20 μL.

Chiral analysis: the detection and analysis are performed by a PerkinElmer Series 200 high performance liquid chromatographic instrument fitted with a UV detector, Chiralcel OD-H chiral column (4.6×250 mm), mobile phase volume ratio of n-hexane:isopropanol:trifluoroacetic acid=80:20: 0.1, the flow rate of 0.5 mL/min, the column temperature of 25° C., the injection volume of 20 μL, and the detection wavelength of 280 nm.

The solubility of Danshensu is low, and if a crystal is separated out during the transformation process, then measured after dilution.

The optical purity of Danshensu is evaluated by the enantiomeric excess value (% e.e).

When producing R-danshensu,
Enantiomeric excess value (% e.e)=[(SR−SS)/(SR+SS)× 100%]
When producing S-danshensu,
Enantiomeric excess value (% e.e)=[(SS−SR)/(SR+SS)× 100%]

Where SS is the peak area of S-danshensu in the transformation liquid, and SR is the peak area in liquid chromatography of R-danshensu in the transformation liquid.

EXAMPLE 1

For the screening of L-glutamate dehydrogenase, various L-glutamate dehydrogenase genes were respectively cloned from various strains and expressed in *E. coli* BL21 (DE3). Method for inducing expression: recombinant *E. coli* was transferred to an LB fermentation medium (peptone 10 g/L, yeast powder 5 g/L, NaCl 10 g/L) in a volume ratio of 2%, when the OD600 of cells reached 0.6-0.8, IPTG was added to a final concentration of 0.4 mM, and culture was performed at 20° C. for 8 h to induce expression. After the induction of expression was completed, the cells were collected by centrifugation at 20° C. and 8000 rpm for 20 minutes.

According to the literature (Cloning, expression and enzyme activity determination of glutamate dehydrogenase gene in *Bacillus natto*. Journal of Shanghai Jiaotong University (Agricultural Science), 2010, 1: 82-86.), the activity of a crude enzyme solution was measured by cell disruption, and the activity of L-glutamate dehydrogenase with NAD as a coenzyme was measured by the method described above. The results were shown in Table 1. Therefore, it is preferred to select the L-glutamate dehydrogenase bsgdh derived from *Bacillus subtilis* for the production of Danshensu.

TABLE 1

Comparison of activities of different L-amino acid dehydrogenases

| Recombinant strain | Activity U/ml |
|---|---|
| *E. coli* BL21(DE3)/pETDuet-1-ecgdh | 0.3 |
| *E. coli* BL21(DE3)/pETDuet-1-rsgdh | 1.1 |
| *E. coli* BL21(DE3)/pETDuet-1-csgdh | 1.6 |
| *E. coli* BL21(DE3)/pETDuet-1-bsgdh | 3.5 |

EXAMPLE 2 hpaD and mhpB on *E. coli* BL21 (DE3) were singly or doubly knocked out according to the method described in the literature (Large scale validation of an efficient CRISPR/Cas-based multi gene editing protocol in *E. coli*. Microbial Cell Factories, 2017, 16(1):68). Wherein, the gene knockout plasmids used in the present disclosure were pCasRed and pCRISPR-gDNA (hpaD sgRNA), which were introduced into *E. coli* BL21 (DE3) together with a homologous arm (hpaD donor), and Cas9/sgRNA induced a double-strand break at the hpaD gene in a host. The recombinant enzyme Red integrated hpaD donor into the hpaD gene to achieve gene knockout and sequencing verification. hpaD sgRNA, hpaD donor, mhpB sgRNA, and mhpB donor were shown in SEQ ID NO: 16, SEQ ID NO: 17, SEQ ID NO: 18, and SEQ ID NO: 19, respectively. mhpB was knocked out in the same way.

A solution with the pH of 7 was prepared, in which the levodopa or D-danshensu was 4 g/L, the wet cell volume was 200 g/L, and the concentration was measured after standing at 35° C. for 10 hours. Table 2 showed the remaining amount of levodopa and D-Danshensu in the reaction system.

TABLE 2

Residual concentrations of different strains after decomposition of substrates and products

| | Levodopa g/L | D-Danshensu g/L |
|---|---|---|
| E. coli BL21(DE3) | 1.5 | 1.5 |
| E. coli BL21(ΔhpaDΔmhpB, DE3) | 3.6 | 3.6 |
| E. coli BL21(ΔhpaD, DE3) | 2.1 | 2.7 |
| E. coli BL21(ΔmhpB, DE3) | 1.6 | 1.6 |

E. coli BL21 (ΔhpaDΔmhpB, DE3) worked best and was named E. coli HM.

EXAMPLE 3

Construction of recombinant E. coli simultaneously expressing α-hydroxycarboxylic acid dehydrogenase, L-amino acid oxidase and exogenous L-glutamate dehydrogenase: the genes encoding tyrosine phenol lyase, L-amino acid oxidase, α-hydroxycarboxylic acid dehydrogenase and L-glutamate dehydrogenase were firstly ligated to a plasmid. A recombinant plasmid co-expressed by the three genes was obtained, which was transformed into E. coli HM, and a positive transformant, i.e. recombinant E. coli, was obtained by screening with an antibiotic plate.

After the induced expression of recombinant E. coli was completed, the strains were collected. A reaction was carried out in a reaction volume of 100 ml at 35° C. for 12 hours, in which the wet cell weight was 40 g/L, the concentration of levodopa was 40 g/L, the concentration of L-glutamic acid was 30 g/L, and pH was 8.0. The yield and configuration of Danshensu were determined by liquid chromatography after the transformation. The results were shown in Table 3.

TABLE 3

Comparison of various recombinant strains

| Recombinant strains | Danshensu Concentration g/L | Configuration | e.e % | α-ketoglutaric acid g/L |
|---|---|---|---|---|
| E. coli HM/pETDuet-1-wcldhl-bsgdh-cmaao | 17.7 | S | >99.9 | 18.4 |
| E. coli HM/pETDuet-1-bcldhl-bsgdh-cmaao | 16.5 | S | >99.9 | 19.4 |
| E. coli HM/pETDuet-1-lfldhl-bsgdh-cmaao | 13.4 | S | >99.9 | 14.2 |
| E. coli HM/pETDuet-1-efmdhd-bsgdh-cmaao | 19.8 | R | >99.9 | 23.2 |
| E. coli HM/pETDuet-1-lpldhd-bsgdh-1-cmaao | 16.4 | R | >99.9 | 18.0 |
| E. coli HM/pETDuet-1-lfldhd-bsgdh-cmaao | 20.1 | R | >99.9 | 19.0 |
| E. coli HM/pETDuet-1-efmdhd-bsgdh-pmaao | 13.2 | R | >99.9 | 14.6 |
| E. coli HM/pETDuet-1-efmdhd-bsgdh-praao | 18.4 | R | >99.9 | 24.9 |
| E. coli HM/pETDuet-1-efmdhd-bsgdh-mmaao | 19.1 | R | >99.9 | 21.3 |
| E. coli HM/pETDuet-1-efmdhd-bsgdh-ilaao | 17.9 | R | >99.9 | 25.3 |
| E. coli HM/pACYCDue-1-lfldhd-bsgdh-cmaao | 20.4 | R | >99.9 | 27.0 |
| E. coli HM/pCOLADuet-1-lfldhd-bsgdh-cmaao | 24.9 | R | >99.9 | 28.6 |
| E. coli HM/pRSFDuet-1-lfldhd-bsgdh-cmaao | 22.0 | R | >99.9 | 25.8 |
| E. coli HM/pCOLADuet-wcldhl-bsgdh-cmaao | 23.7 | S | >99.9 | 28.5 |

Construction of recombinant E. coli simultaneously expressing α-hydroxycarboxylic acid dehydrogenase, L-amino acid oxidase and exogenous L-lactate dehydrogenase: the genes encoding L-amino acid oxidase, α-hydroxycarboxylic acid dehydrogenase, and L-lactate dehydrogenase were firstly ligated to the pETDuet-1 or pACYCDuet-1 plasmid. A recombinant plasmid co-expressed by the three genes was obtained, which was transformed into E. coli HM, and a positive transformant, i.e. recombinant E. coli, was obtained by screening with chloramphenicol and ampicillin plates.

After the induced expression of recombinant E. coli was completed, the strains were collected. A reaction was carried out in a reaction volume of 100 ml at 35° C. for 12 hours, in which the wet cell weight was 40 g/L, the concentration of levodopa was 40 g/L, the concentration of L-lactic acid was 30 g/L, and pH was 8.0. The yield and configuration of Danshensu were determined by liquid chromatography after the transformation. The results were shown in Table 4.

TABLE 4

Comparison of various recombinant strains

| Recombinant strains | Danshensu | | | pyruvic acid g/L |
|---|---|---|---|---|
| | Concentration g/L | Configuration | e.e % | |
| E. coli HM/pETDuet-1-wcldhl-llldh-cmaao | 17.9 | S | >99.9 | 9.2 |
| E. coli HM/pETDuet-1-bcldhl-llldh-cmaao | 8.4 | S | >99.9 | 5.3 |
| E. coli HM/pETDuet-1-lfldhl-llldh-cmaao | 3.7 | S | >99.9 | 2.2 |
| E. coli HM/pETDuet-1-efmdhd-llldh-cmaao | 19.8 | R | >99.9 | 11.4 |
| E. coli HM/pETDuet-1-lpldhd-llldh-1-cmaao | 3.4 | R | >99.9 | 2.0 |
| E. coli HM/pETDuet-1-efmdhd-llldh-pmaao | 17.6 | R | >99.9 | 9.5 |
| E. coli HM/pETDuet-1-efmdhd-llldh-praao | 18.2 | R | >99.9 | 12.3 |
| E. coli HM/pETDuet-1-efmdhd-llldh-mmaao | 17.3 | R | >99.9 | 11.6 |
| E. coli HM/pETDuet-1-efmdhd-llldh-ilaao | 18.7 | R | >99.9 | 13.0 |
| E. coli HM/pACYCDue-1-efmdhd-llldh-cmaao | 19.5 | R | >99.9 | 13.5 |
| E. coli HM/pCOLADuet-1-efmdhd-llldh-cmaao | 22.3 | R | >99.9 | 14.3 |
| E. coli HM/pRSFDuet-1-efmdhd-llldh-cmaao | 20.1 | R | >99.9 | 12.1 |
| E. coli HM/pCOLADuet-wcldh1-llldh-cmaao | 21.7 | S | >99.9 | 14.8 |

Construction of recombinant E. coli simultaneously expressing α-hydroxycarboxylic acid dehydrogenase, L-amino acid oxidase, tyrosine phenol lyase and L-lactate dehydrogenase: the genes encoding tyrosine phenol lyase, L-amino acid oxidase, α-hydroxycarboxylic acid dehydrogenase, and L-lactate dehydrogenase were firstly ligated to the pETDuet-1 or pACYCDuet-1 plasmid, respectively. Two recombinant plasmids co-expressed by two genes were obtained, which were transformed into E. coli HM, and a positive transformant, i.e. recombinant E. coli, was obtained by screening with chloramphenicol and ampicillin plates.

After the induced expression of recombinant E. coli was completed, the strains were collected. A reaction was carried out in a reaction volume of 100 ml at 35° C. for 12 hours, in which the wet cell weight was 20 g/L, the concentration of catechol was 10 g/L, the concentration of L-lactic acid was 10 g/L, pH was 8.0, and the concentration of ammonium ion was 30 g/L. The yield and configuration of Danshensu were determined by liquid chromatography after the transformation. The results were shown in Table 5.

ligated to the pETDuet-1 or pACYCDuet-1 plasmid. Recombinant plasmids co-expressed by the three genes were obtained, which were transformed into E. coliHM, and a positive transformant, i.e. recombinant E. coli, were obtained by screening with chloramphenicol and ampicillin plates.

Method for inducing expression: recombinant E. coli was transferred to an LB fermentation medium (peptone 10 g/L, yeast powder 5 g/L, NaCl 10 g/L) in a volume ratio of 2%, when the OD600 of cells reached 0.6-0.8, IPTG was added to a final concentration of 0.4 mM, and culture was performed at 20° C. for 8 h to induce expression. After the induction of expression was completed, the cells were collected by centrifugation at 20° C. and 8000 rpm for 20 minutes.

After the induced expression of recombinant E. coli was completed, the strains were collected. A reaction was carried out in a reaction volume of 100 ml at 35° C. for 12 hours,

TABLE 5

Comparison of various recombinant strains

| Recombinant strains | Danshensu | | |
|---|---|---|---|
| | Concentration g/L | Configuration | e.e % |
| E. coli HM/pETDuet-1-wcldhl-llldh + pACYCDuet-1-cmaao-ehtpl | 8.5 | S | >99.9 |
| E. coli HM/pETDuet-1-cmaao-cftpl + pACYCDuet-1-wcldhl-llldh | 7.2 | S | >99.9 |
| E. coli HM/pETDuet-1-mmaao-ehtpl + pACYCDuet-1-bcldhl-llldh | 7.3 | S | >99.9 |
| E. coli HM/pETDuet-1-bcldhl-llldh + pACYCDuet-1-mmaao-ehtpl | 4.7 | S | >99.9 |
| E. coli HM/pETDuet-1-lfldhl-llldh + pACYCDuet-1-praao-ehtpl | 2.2 | S | >99.9 |
| E. coli HM/pETDuet-1-efmdhd-llldh + pACYCDuet-1-cmaao-ehtpl | 8.1 | R | >99.9 |
| E. coli HM/pETDuet-1-cmaao-ehtpl + pACYCDuet-1-efmdhd-llldh | 6.1 | R | >99.9 |
| E. coli HM/pETDuet-1-efmdhd-llldh + pACYCDuet-1-cmaao-ehtpl | 7.7 | R | >99.9 |
| E. coli HM/pETDuet-1-lpldhd-llldh + pACYCDuet-1-pmaao-ehtpl | 1.4 | R | >99.9 |
| E. coli HM/pETDuet-1-lfldhd-llldh + pACYCDuet-1-ilaao-aptpl | 5.8 | R | >99.9 |

Construction of recombinant E. coli simultaneously expressing α-hydroxycarboxylic acid dehydrogenase, L-amino acid oxidase, and glucose dehydrogenase: the genes encoding L-amino acid oxidase, α-hydroxycarboxylic acid dehydrogenase, and glucose dehydrogenase were firstly in which the wet cell weight was 40 g/L, the concentration of levodopa was 40 g/L, the concentration of glucose was 30 g/L, and pH was 8.0. The yield and configuration of Danshensu were determined by liquid chromatography after the transformation. The results were shown in Table 6.

TABLE 6

Comparison of various recombinant strains

| Recombinant strains | Danshensu Concentration g/L | Configuration | e.e % |
|---|---|---|---|
| E. coli HM/pETDuet-1-wcldhl-bsgdh-cmaao | 25.7 | S | >99.9 |
| E. coli HM/pETDuet-1-bcldhl-bsgdh-cmaao | 20.5 | S | >99.9 |
| E. coli HM/pETDuet-1-lfldhl-bsgdh-cmaao | 24.4 | S | >99.9 |
| E. coli HM/pETDuet-1-efmdhd-bsgdh-cmaao | 26.5 | R | >99.9 |
| E. coli HM/pETDuet-1-lpldhd-bsgdh-1-cmaao | 24.6 | R | >99.9 |
| E. coli HM/pETDuet-1-efmdhd-bsgdh-pmaao | 19.7 | R | >99.9 |
| E. coli HM/pETDuet-1-efmdhd-bsgdh-praao | 24.4 | R | >99.9 |
| E. coli HM/pETDuet-1-efmdhd-bsgdh-mmaao | 25.5 | R | >99.9 |
| E. coli HM/pETDuet-1-efmdhd-bsgdh-ilaao | 27.3 | R | >99.9 |
| E. coli HM/pACYCDue-1-efmdhd-bsgdh-cmaao | 24.1 | R | >99.9 |
| E. coli HM/pCOLADuet-1-efmdhd-bsgdh-cmaao | 20.8 | R | >99.9 |
| E. coli HM/pRSFDuet-1-efmdhd-bsgdh-cmaao | 23.8 | R | >99.9 |
| E. coli HM/pCOLADuet-wcldhl-bsgdh-cmaao | 20.0 | S | >99.9 |

TABLE 7

Correspondence of primer name and SEQ ID NO

| Name | SEQ ID NO |
|---|---|
| gltS sgRNA | SEQ ID NO: 1 |
| gltS-FF | SEQ ID NO: 3 |
| gltS-FR | SEQ ID NO: 4 |
| gltS-gpdA-F | SEQ ID NO: 5 |
| gltS-gpdA-R | SEQ ID NO: 6 |
| gltS-RF | SEQ ID NO: 7 |
| gltS-RR | SEQ ID NO: 8 |

Expression was induced according to the method described in Example 1, and various types of cells were collected for transformation analysis, and the results were shown in Table 8. The whole cell transformation system in the transformation system was: wet cell weight 5 g/L, L-glutamic acid 50 g/L, levodopa 20 g/L, pH 8.0, temperature 40° C., shaker speed 250 rpm; transformation time 12 hours.

TABLE 8

Comparison of transformation results

| Recombinant strains | Danshensu g/L Concentration g/L | Configuration | e.e % | α-ketoglutaric acid g/L |
|---|---|---|---|---|
| E. coli HM (PG-gltS)/pCOLADuet-1-lfldhd-bsgdh-cmaao | 6.8 | R | >99.9 | 7.2 |
| E. coli HM (PG-gltS)/pCOLADuet-1-wcldhl-bsgdh-cmaao | 7.2 | S | >99.9 | 7.8 |
| E. coli HM/pCOLADuet-1-lfldhd-bsgdh-cmaao | 5.6 | R | >99.9 | 5.9 |
| E. coli HM/pCOLADuet-1-wcldhl-bsgdh-cmaao | 5.3 | S | >99.9 | 5.7 |

EXAMPLE 4

A constitutive promoter (PG) having medium expression intensity in front of glyceraldehyde-3-phosphate dehydrogenase gene (gpdA) in E. coli was added in front of the corresponding gene on the E. coli HM genome using the method described in the literature Large scale validation of an efficient CRISPR/Cas-based multi gene editing protocol in E. coli. Microbial Cell Factories, 2017,16(1):68, and the sequence was shown in SEQ ID NO: 15.

When the expression of the gene gltS was enhanced, the E. coli HM genome was used as a template, the upstream, promotor and downstream sequences were amplified with the primers gltS-FF/gltS-FR, gltS-gpdA-F/gltS-gpdA-R, and gltS-RF/gltS-RR, and were fused using gltS-FF and gltS-RR as primers to obtain an expression cassette containing the gpdA promoter. Then, after transforming into E. coli HM together with the plasmid pCasRed and pC CRISPR-gDNA (containing gltS sgRNA), the Cas9/sgRNA induced a double-strand break at the gltS gene of the host, and the recombinase Red integrated the gpdA promoter in front of the gltS gene. Sequencing verification was then carried out.

Table 7 below showed the corresponding indexes of the primer name and SEQ ID NO.

The best-performing E. coli HM (PG-gltS) was named E. coli HML-1.

When the expression of the gene lldP was enhanced, the upstream, promoter and downstream sequences were amplified by using the E. coli HM genome as a template, and an expression cassette containing the gpdA promoter was obtained. Then, after transforming into E. coli HM together with plasmid pCasRed and pCRISPR-gDNA (including lldP sgRNA), Cas9/sgRNA induced a double-strand break at the lldP gene of a host, and recombinase Red integrated the gpdA promoter in front of lldP gene. Sequencing verification was then carried out.

Expression was induced according to the method described in Example 2, and various types of cells were collected for transformation analysis, and the results were shown in Table 9. The whole cell transformation system in the transformation system was: wet cell weight 5 g/L, L-lactic acid 50 g/L, levodopa 20 g/L, pH 8.0, temperature 40° C., shaker speed 250 rpm; transformation time 12 hours.

TABLE 9

Comparison of transformation results

| Recombinant strains | Danshensu Concentration g/L | Configuration | e.e % | Pyruvic acid g/L |
|---|---|---|---|---|
| E. coli HM (PG-lldP)/pCOLADuet-1-efmdhd-llldh-cmaao | 6.4 | R | >99.9 | 5.1 |
| E. coli HM (PG-lldP)/pCOLADuet-1-wcldhl-llldh-cmaao | 7.2 | S | >99.9 | 4.8 |
| E. coli HM/pCOLADuet-1-efmdhd-llldh-cmaao | 4.9 | R | >99.9 | 3.2 |
| E. coli HM/pCOLADuet-1-wcldhl-llldh-cmaao | 5.8 | S | >99.9 | 3.9 |

The best-performing E. coli HM (PG-lldP) was named E. coli HML-2.

When the expression of the gene hpaX was enhanced, the upstream, promoter and downstream sequences were firstly amplified using a method similar to that for enhancing the expression of the gene lldP, and the primers were designed to be fused to obtain an expression cassette containing the gpdA promoter. Then, after transfecting into E. coli HM together with plasmid pCasRed and pCRISPR-gDNA (including hpaX sgRNA), Cas9/sgRNA induced a double-strand break at the hpaX gene of a host, and recombinase Red integrated the gpdA promoter in front of hpaX gene. Sequencing verification was then carried out.

When the expression of the gene mhpT was enhanced, the upstream, promoter and downstream sequences were firstly amplified using a method similar to that for enhancing the expression of the gene lldP, and the primers were designed to be fused to obtain an expression cassette containing the gpdA promoter. Then, after transforming into E. coli HM together with plasmid pCasRed and pCRISPR-gDNA (including mhpT sgRNA), Cas9/sgRNA induced a double-strand break at the mhpT gene of a host, and recombinase Red integrated the gpdA promoter in front of mhpT gene. Sequencing verification was then carried out.

Expression was induced according to the method described in Example 2, and various types of cells were collected for transformation analysis, and the results were shown in Table 10. The whole cell transformation system in the transformation system was: wet cell weight 10 g/L, L-lactic acid 200 g/L, catechol 10 g/L, pH 8.0, temperature 40° C., shaker speed 250 rpm; transformation time 12 hours.

The best-performing E. coli HM (PG-lldP,PG-hpaX,PG-mhpT) was named E. coli HMLHM.

EXAMPLE 5

A constitutive promoter (PG) having medium expression intensity in front of glyceraldehyde-3-phosphate dehydrogenase gene (gpdA) in E. coli was added in front of the genes nadA and ribF in E. coli HML according to the method in Example 4, and the sequence was shown in SEQ ID NO: 15. The plasmid was then introduced.

When the expression of the gene nadA was enhanced, the E. coli HML genome was used as a template, the upstream, promotor and downstream sequences were amplified with the primers nadA-FF/nadA-FR, nadA-gpdA-F/nadA-gpdA-R, and nadA-RF/nadA-RR, and were fused using nadA-FF and nadA-RR as primers to obtain an expression cassette containing the gpdA promoter. Then, after transforming into E. coli HML together with the plasmid pCasRed and pCRISPR-gDNA (containing nadA sgRNA), the Cas9/sgRNA induced a double-strand break at the nadA gene of a host, and the recombinase Red integrated the gpdA promoter in front of the nadA gene. Sequencing verification was then carried out.

When the expression of the gene ribF was enhanced, the E. coli HML genome was used as a template, and the upstream, promotor and downstream sequences were amplified with the primers ribF-FF/ribF-FR, ribF-gpdA-F/ribF-gpdA-R, and ribF-RF/ribF-RR, and were fused using ribF-FF and ribF-RR as primers to obtain an expression cassette containing the gpdA promoter. Then, after transforming into

TABLE 10

Comparison of transformation results

| Recombinant strains | Danshensu g/L Concentration g/L | Configuration | e.e % |
|---|---|---|---|
| E. coli HM (PG-lldP)/pETDuet-1-wcldhl-llldh + pACYCDuet-1-cmaao-ehtpl | 6.9 | S | >99.9 |
| E. coli HM (PG-hpaX)/pETDuet-1-wcldhl-llldh + pACYCDuet-1-cmaao-ehtpl | 5.9 | S | >99.9 |
| E. coli HM (PG-mhpT)/pETDuet-1-wcldhl-llldh + pACYCDuet-1-cmaao-ehtpl | 5.3 | S | >99.9 |
| E. coli HM (PG-hpaX, PG-mhpT)/pETDuet-1-wcldhl-llldh + pACYCDuet-1-cmaao-ehtpl | 6.8 | S | >99.9 |
| E. coli HM (PG-lldP, PG-hpaX, PG-mhpT)/pETDuet-1-wcldhl-llldh + pACYCDuet-1-cmaao-ehtpl | 7.8 | S | >99.9 |
| E. coli HM (PG-lldP, PG-hpaX, PG-mhpT)/pETDuet-1-wcldhl-llldh + pACYCDuet-1-cmaao-ehtpl | 8.0 | S | >99.9 |
| E. coli HM/pETDuet-1-wcldhl-llldh + pACYCDuet-1-cmaao-ehtpl | 4.8 | S | >99.9 |
| E. coli HM/pETDuet-1-efmdhd-llldh + pACYCDuet-1-cmaao-ehtpl | 5.4 | R | >99.9 |

E. coli HML together with the plasmid pCasRed and pCRISPR-gDNA (containing ribF sgRNA), the Cas9/sgRNA induced a double-strand break at the ribF gene of a host, and the recombinase Red integrated the gpdA promoter in front of the ribF gene. Sequencing verification was then carried out.

Table 11 below showed the corresponding indexes of the primer name and SEQ ID NO.

TABLE 11 correspondence of primer name and SEQ ID NO

| Name | SEQ ID NO |
|---|---|
| ribF sgRNA | SEQ ID NO: 20 |
| nadA sgRNA | SEQ ID NO: 2 |
| ribF-FF | SEQ ID NO: 21 |
| ribF-FR | SEQ ID NO: 22 |
| ribF-gpdA-F | SEQ ID NO: 23 |
| ribF-gpdA-R | SEQ ID NO: 24 |
| ribF-RF | SEQ ID NO: 25 |
| ribF-RR | SEQ ID NO: 26 |

TABLE 11-continued correspondence of primer name and SEQ ID NO

| Name | SEQ ID NO |
|---|---|
| nadA-FF | SEQ ID NO: 9 |
| nadA-FR | SEQ ID NO: 10 |
| nadA-gpdA-F | SEQ ID NO: 11 |
| nadA-gpdA-R | SEQ ID NO: 12 |
| nadA-RF | SEQ ID NO: 13 |
| nadA-RR | SEQ ID NO: 14 |

After the genetic modification was completed, the co-expression plasmid was introduced. Expression was induced according to the method described in Example 1, various types of cells were collected for transformation analysis, and the results were shown in Table 12. The whole cell transformation system in the transformation system was: wet cell weight 20 g/L, L-glutamic acid 120 g/L, levodopa 120 g/L, pH 9.0, temperature 30° C., shaker speed 250 rpm; transformation time 24 hours. The comparison of transformation results were shown in Table 12.

TABLE 12

Comparison of transformation results

| Strains | Danshensu g/L | | | α-Ketoglutaric acid g/L |
|---|---|---|---|---|
| | Concentration g/L | Configuration | e.e % | |
| E. coli HML(PG-ribF, PG-nadA)/pCOLADuet-1-lfldhd-bsgdh-cmaao | 91.6 | R | >99.9 | 97.2 |
| E. coli HML(PG-ribF, PG-nadA)/pCOLADuet-1-wcldhl-bsgdh-cmaao | 95.0 | S | >99.9 | 96.1 |
| E. coli HML(PG-ribF)/pCOLADuet-1-efmdhd-bsgdh-cmaao | 73.3 | R | >99.9 | 77.4 |
| E. coli HML(PG-nadA)/pCOLADuet-1-lfldhd-bsgdh-cmaao | 81.5 | R | >99.9 | 87.2 |
| E. coli HML/pCOLADuet-1-lfldhd-bsgdh-cmaao | 66.0 | R | >99.9 | 69.1 |
| E. coli HML/pCOLADuet-1-wcldhl-bsgdh-cmaao | 69.3 | S | >99.9 | 73.5 |

The best-performing E. coli HML (PG-nadA,PG-ribF) was named E. coli HNR-1.

After the genetic modification was completed, the co-expression plasmid was introduced. Expression was induced according to the method described in Example 1, various types of cells were collected for transformation analysis, and the results were shown in Table 7. The whole cell transformation system in the transformation system was: wet cell weight 20 g/L, L-lactic acid 100 g/L, levodopa 120 g/L, pH 9.0, temperature 30° C., shaker speed 250 rpm; transformation time 24 hours. The comparison of transformation results were as shown in Table 13.

TABLE 13

Comparison of transformation results

| Strains | Danshensu | | | Pyruvic acid g/L |
|---|---|---|---|---|
| | Concentration g/L | Configuration | e.e % | |
| E. coli HML(PG-ribF, PG-nadA)/pCOLADuet-1-efmdhd-llldh-cmaao | 92.1 | R | >99.9 | 50.2 |
| E. coli HML(PG-ribF, PG-nadA)/pCOLADuet-1-wcldhl-llldh-cmaao | 94.5 | S | >99.9 | 51.3 |
| E. coli HML(PG-ribF)/pCOLADuet-1-efmdhd-llldh-cmaao | 74.2 | R | >99.9 | 42.3 |

TABLE 13-continued

| | Comparison of transformation results | | | |
|---|---|---|---|---|
| | | Danshensu | | |
| Strains | Concentration g/L | Configuration | e.e % | Pyruvic acid g/L |
| E. coli HML(PG-nadA)/pCOLADuet-1-efmdhd-llldh-cmaao | 83.2 | R | >99.9 | 47.2 |
| E. coli HML/pCOLADuet-1-efmdhd-llldh-cmaao | 66.7 | R | >99.9 | 39.6 |
| E. coli HML/pCOLADuet-1-wcldhl-llldh-cmaao | 69.3 | S | >99.9 | 37.1 |

The best-performing E. coli HML (PG-nadA,PG-ribF) was named E. coli HNR-2.

After the genetic modification was completed, the co-expression plasmid was introduced. Expression was induced according to the method described in Example 1, various types of cells were collected for transformation analysis, and the results were shown in Table 14. The whole cell transformation system in the transformation system was: wet cell weight 20 g/L, L-lactic acid 200 g/L, catechol 200 g/L, pH 9.0, temperature 30° C., shaker speed 250 rpm; transformation time 24 hours.

TABLE 14

| | Comparison of transformation results | | |
|---|---|---|---|
| | | Danshensu | |
| Strains | Concentration g/L | Configuration | e.e % |
| E. coli HMLHM(PG-ribF, PG-nadA)/pETDuet-1-wcldhl-llldh + pACYCDuet-1-cmaao-ehtpl | 87.2 | S | >99.9 |
| E. coli HMLHM(PG-ribF)/pETDuet-1-wcldhl-llldh + pACYCDuet-1-cmaao-ehtpl | 66.9 | S | >99.9 |
| E. coli HMLHM(PG-nadA)/pETDuet-1-wcldhl-llldh + pACYCDuet-1-cmaao-ehtpl | 84.9 | S | >99.9 |
| E. coli HMLHM(PG-nadA, PG-pdxJ)/pETDuet-1-wcldhl-llldh + pACYCDuet-1-cmaao-ehtpl | 91.3 | S | >99.9 |
| E. coli HMLHM(PG-nadA, PG-ribF, PG-pdxJ)/pETDuet-1-wcldhl-llldh + pACYCDuet-1-cmaao-ehtpl | 94.5 | S | >99.9 |
| E. coli HMLHM/pETDuet-1-wcldhl-llldh + pACYCDuet-1-cmaao-ehtpl | 56.0 | S | >99.9 |
| E. coli HMLHM(PG-ribF, PG-nadA)/pETDuet-1-efmdhd-llldh + pACYCDuet-1-cmaao-ehtpl | 85.7 | R | >99.9 |
| E. coli HMLHM(PG-ribF)/pETDuet-1-efmdhd-llldh + pACYCDuet-1-cmaao-ehtpl | 58.5 | R | >99.9 |
| E. coli HMLHM(PG-nadA)/pETDuet-1-efmdhd-llldh + pACYCDuet-1-cmaao-ehtpl | 86.4 | R | >99.9 |
| E. coli HMLHM(PG-nadA, PG-pdxJ)/pETDuet-1-efmdhd-llldh + pACYCDuet-1-cmaao-ehtpl | 90.7 | R | >99.9 |
| E. coli HMLHM(PG-nadA, PG-ribF, PG-pdxJ)/pETDuet-1-efmdhd-llldh + pACYCDuet-1-cmaao-ehtpl | 96.4 | R | >99.9 |
| E. coli HMLHM/pETDuet-1-efmdhd-llldh + pACYCDuet-1-cmaao-ehtpl | 60.4 | R | >99.9 |

The best-performing E. coli HMLHM (PG-nadA,PG-ribF, PG-pdxJ) was named E. coli NPR.

After the genetic modification was completed, the co-expression plasmid was introduced. Expression was induced according to the method described in Example 1, various types of cells were collected for transformation analysis, and the results were shown in Table 15. The whole cell transformation system in the transformation system was: wet cell weight 20 g/L, glucose 100 g/L, levodopa 120 g/L, pH 9.0, temperature 30° C., shaker speed 250 rpm; transformation time 24 hours.

TABLE 15

Comparison of transformation results

| Strains | Danshensu g/L Concentration g/L | Configuration | e.e % |
|---|---|---|---|
| E. coli HM(PG-ribF, PG-nadA)/pCOLADuet-1-efmdhd-bsgdh-cmaao | 95.6 | R | >99.9 |
| E. coli HM(PG-ribF, PG-nadA)/pCOLADuet-1-wcldhl-bsgdh-cmaao | 98.3 | S | >99.9 |
| E. coli HM(PG-ribF)/pCOLADuet-1-efmdhd-bsgdh-cmaao | 86.1 | R | >99.9 |
| E. coli HM(PG-nadA)/pCOLADuet-1-efmdhd-bsgdh-cmaao | 88.9 | R | >99.9 |
| E. coli HM/pCOLADuet-1-efmdhd-bsgdh-cmaao | 75.0 | R | >99.9 |
| E. coli HM/pCOLADuet-1-wcldhl-bsgdh-cmaao | 79.4 | S | >99.9 |

The best-performing E. coli HML (PG-nadA,PG-ribF) was named E. coli NR.

EXAMPLE 6

According to the method for inducing expression as described in Example 1, after the induced expression of E. coli HNR/pCOLADuet-1-efmdhd-bsgdh-cmaao was completed, the strains were collected. The wet cell weight was 1 g/L, L-glutamic acid was 1 g/L, levodopa was 1 g/L, pH 6.0, temperature was 15° C., and the shaker speed was 250 rpm in a 100 ml reaction system; transformation time was 1 hour. As a result of the measurement, the concentration of R-danshensu was 93 mg/L, and e.e %>99.9.

According to the method for inducing expression as described in Example 1, after the induced expression of E. coli HNR/pCOLADuet-1-efmdhd-llldh-cmaao was completed, the strains were collected. The wet cell weight was 1 g/L, L-lactic acid was 1 g/L, levodopa was 1 g/L, pH 6.0, temperature was 15° C., and the shaker speed was 250 rpm in a 100 ml reaction system; transformation time was 1 hour. As a result of the measurement, the concentration of R-danshensu was 93 mg/L, and e.e %>99.9.

According to the method for inducing expression as described in Example 1, after the induced expression of E. coli NPR/pETDuet-1-wcldhl-llldh+pACYCDuet-1-cmaao-ehtpl was completed, the strains were collected. The wet cell weight was 1 g/L, L-lactic acid was 1 g/L, catechol was 1 g/L, pH 6.0, temperature was 15° C., and the shaker speed was 250 rpm in a 100 ml reaction system; transformation time was 1 hour. As a result of the measurement, the concentration of S-danshensu was 78 mg/L.

According to the method for inducing expression as described in Example 1, after the induced expression of E. coli NR/pCOLADuet-1-efmdhd-bsgdh-cmaao was completed, the strains were collected. The wet cell weight was 1 g/L, glucose was 1 g/L, levodopa was 1 g/L, pH 6.0, temperature was 15° C., and the shaker speed was 250 rpm in a 100 ml reaction system; transformation time was 1 hour. As a result of the measurement, the concentration of S-danshensu was 93 mg/L and e.e %>99.9.

EXAMPLE 7

According to the method for inducing expression as described in Example 1, after the induced expression of the strains in Table 16 was completed, the strains were collected. The wet cell weight was 200 g/L, L-glutamic acid was 200 g/L, levodopa was 200 g/L, pH 8.5, temperature was 40° C., and the shaker speed was 250 rpm in a 100 ml reaction system; transformation time was 48 hours. The results were measured after all the precipitates were diluted and dissolved, and the results were shown in Table 16.

TABLE 16

Comparison of transformation results

| Strains | Danshensu Yield g/L | Configuration | e.e % | α-ketoglutaric acid g/L |
|---|---|---|---|---|
| E. coli HNR/pCOLADuet-1-lfldhd-bsgdh-cmaao | 183 | R | >99.9 | 184 |
| E. coli HNR/pCOLADuet-1-wcldhl-bsgdh-cmaao | 184 | S | >99.9 | 189 |
| E. coli HNR/pCOLADuet-1-lfldhd-bsgdh-pmaao | 131 | R | >99.9 | 130 |
| E. coli HNR/pCOLADuet-1-lfldhd-bsgdh-praao | 159 | R | >99.9 | 171 |
| E. coli HNR/pCOLADuet-1-wcldhl-bsgdh-mmaao | 140 | S | >99.9 | 152 |
| E. coli HNR/pCOLADuet-1-wcldhl-bsgdh-praao | 148 | S | >99.9 | 155 |

According to the method for inducing expression as described in Example 1, after the induced expression of the strains in Table 17 was completed, the strains were collected. The wet cell weight was 200 g/L, L-lactic acid was 200 g/L, levodopa was 200 g/L, pH 8.5, temperature was 40° C., and the shaker speed was 250 rpm in a 100 ml reaction system; transformation time was 48 hours. The results were measured after all the precipitates were diluted and dissolved.

TABLE 17

Comparison of transformation results

| Strains | Danshensu Yield g/L | Configuration | e.e % | Pyruvic acid g/L |
|---|---|---|---|---|
| E. coli HNR/pCOLADuet-1-efmdhd-llldh-cmaao | 188 | R | >99.9 | 112 |
| E. coli HNR/pCOLADuet-1-wcldhl-llldh-cmaao | 186 | S | >99.9 | 108 |

TABLE 17-continued

Comparison of transformation results

| Strains | Danshensu Yield g/L | Config- uration | e.e % | Pyruvic acid g/L |
|---|---|---|---|---|
| E. coli NPR/pCOLADuet-1-efmdhd-llldh-pmaao | 132 | R | >99.9 | 74 |
| E. coli HNR/pCOLADuet-1-efmdhd-llldh-praao | 162 | R | >99.9 | 93 |
| E. coli HNR/pCOLADuet-1-wcldhl-llldh-mmaao | 143 | S | >99.9 | 86 |
| E. coli HNR/pCOLADuet-1-wcldhl-llldh-praao | 146 | S | >99.9 | 90 |

According to the method for inducing expression as described in Example 1, after the induced expression of the strains in Table 18 was completed, the strains were collected. The wet cell weight was 200 g/L, L-lactic acid was 200 g/L, catechol was 200 g/L, pH 8.5, temperature was 40° C., and the shaker speed was 250 rpm in a 100 ml reaction system; transformation time was 48 hours. The results were measured after all the precipitates were diluted and dissolved.

TABLE 18

Comparison of transformation results

| Strains | Danshensu Concentration g/L | Configuration | e.e % |
|---|---|---|---|
| E. coli NPR/pETDuet-1-efmdhd-llldh + pACYCDuet-1-cmaao-ehtpl | 382 | R | >99.9 |
| E. coli NPR/pETDuet-1-wcldhl-llldh + pACYCDuet-1-cmaao-ehtpl | 378 | S | >99.9 |
| E. coli NPR/pETDuet-1-efmdhd-llldh + pACYCDuet-1-pmaao-ehtpl | 344 | R | >99.9 |
| E. coli NPR/pETDuet-1-efmdhd-llldh + pACYCDuet-1-ilaao-ehtpl | 348 | R | >99.9 |
| E. coli NPR/pETDuet-1-efmdhd-llldh + pACYCDuet-1-mmaao-ehtpl | 306 | R | >99.9 |
| E. coli NPR/pETDuet-1-efmdhd-llldh + pACYCDuet-1-praao-ehtpl | 333 | R | >99.9 |

According to the method for inducing expression as described in Example 1, after the induced expression of the strains in Table 19 was completed, the strains were collected. The wet cell weight was 200 g/L, glucose was 200 g/L, levodopa was 200 g/L, pH 8.5, temperature was 40° C., and the shaker speed was 250 rpm in a 100 ml reaction system; transformation time was 48 hours. The results were measured after all the precipitates were diluted and dissolved.

TABLE 19

Comparison of transformation results

| Strains | Danshensu Yield g/L | Config- uration | e.e % |
|---|---|---|---|
| E. coli NR/pCOLADuet-1-efmdhd-bsgdh-cmaao | 187.4 | R | >99.9 |
| E. coli NR/pCOLADuet-1-wcldhl-bsgdh-cmaao | 192.6 | S | >99.9 |
| E. coli PR/pCOLADuet-1-efmdhd-bsgdh-pmaao | 134.2 | R | >99.9 |
| E. coli NR/pCOLADuet-1-efmdhd-bsgdh-praao | 174.7 | R | >99.9 |
| E. coli NR/pCOLADuet-1-wcldhl-bsgdh-mmaao | 155.6 | S | >99.9 |
| E. coli NR/pCOLADuet-1-wcldhl-bsgdh-praao | 171.0 | S | >99.9 |

The modification and construction of the above-mentioned enzymes and the co-expressed genetic engineering strains thereof, the culture medium composition and culture method of the strains and the whole cell biotransformation are only preferred examples of the present disclosure, and are not intended to limit the present disclosure. Theoretically, other bacteria, filamentous fungi, actinomycetes, and animal cells can be genetically modified and used for multi-gene co-expressed whole-cell catalysis. Any modifications and equivalents made within the principles and spirit of the present disclosure.

What is claimed is:

1. A recombinant *Escherichia coli* (*E. coli*), wherein the recombinant *E. coli* simultaneously expresses an α-hydroxycarboxylic acid dehydrogenase and an L-amino acid oxidase,
   wherein the recombinant *E. coli* expresses any one or more of: an exogenous L-glutamate dehydrogenase, an exogenous L-lactate dehydrogenase, a glucose dehydrogenase, and a tyrosine phenol lyase,
   wherein when the recombinant *E. coli* expresses tyrosine phenol lyase and L-lactate dehydrogenase, the tyrosine phenol lyase and the L-lactate dehydrogenase are simultaneously expressed;
   wherein the α-hydroxycarboxylic acid dehydrogenase is from *Lactobacillus plantarum*, *Enterococcus faecalis*, or *Lactobacillus fermentum*;
   wherein the L-amino acid oxidase is expressed from any one or more of the gene of: pmaao from *Proteus mirabilis*, cmaao from *Cosenzaea myxofaciens*, praao from *Providencia rettgeri*, mmaao from *Morganella morganii*, and ilaao from *Ignatzschineria larvae*;
   wherein the L-glutamate dehydrogenase is from *E. coli*, *Rhodobacter sphaeroides*, *Clostridium symbiosum*, or *Bacillus subtilis*;
   wherein the L-lactate dehydrogenase is from *Lactococcus lactis*;
   wherein the glucose dehydrogenase is from *Bacillus subtilis*;
   wherein the tyrosine phenol lyase is from *Erwinia herbicola*; and
   wherein the recombinant *E. coli* comprises a gene knock-out of hpaD and mhpB.

2. The recombinant *E. coli* according to claim 1, wherein the recombinant *E. coli* further comprises a constitutive promoter upstream of and operatively linked to a gene with enhanced expression,
   wherein the gene with enhanced expression is expressed in the recombinant *E. coli*,
   wherein the constitutive promoter enhances expression of the gene with enhanced expression;
   wherein the gene with enhanced expression is selected from one or more of: an *E. coli* glutamate transporter gene gltS, an *E. coli* lactate transporter gene lldP, an *E. coli* catechol transporter gene hpaX, an *E. coli* NAD synthesis gene nadA, and an *E. coli* FAD synthesis gene ribF;
   wherein when the recombinant *E. coli* expresses the catechol transporter gene hpaX and the lactate transporter gene lldP, the catechol transporter gene hpaX and the lactate transporter gene lldP are expressed simultaneously, and
   wherein when the recombinant *E. coli* expresses the glutamate transporter gene gltS and the lactate transporter gene lldP, the glutamate transporter gene gtlS and the lactate transporter gene lldP are expressed at different times.

3. The recombinant *E. coli* according to claim 2, wherein the gene with enhanced expression is any one or more of gltS, nadA, and ribF.

4. The recombinant *E. coli* according to claim 2, wherein the gene with enhanced expression is any one or more of lldP, nadA, and ribF.

5. The recombinant *E. coli* according to claim 2, wherein the gene with enhanced expression is any one or more of *E. coli* genes lldP, hpaX, mhpT, nadA, pdxJ, and ribF.

6. The recombinant *E. coli* according to claim 1, wherein the L-glutamate dehydrogenase, L-lactate dehydrogenase, glucose dehydrogenase, tyrosine phenol lyase, L-lactate dehydrogenase, α-hydroxycarboxylic acid dehydrogenase, and L-amino acid oxidase are all co-expressed.

7. The recombinant *E. coli* according to claim 1, wherein the recombinant *E. coli* is *E. coli* strain BL21.

* * * * *